United States Patent
Su et al.

(10) Patent No.: US 8,114,988 B2
(45) Date of Patent: Feb. 14, 2012

(54) PHOSPHORUS-CONTAINING BENZOXAZINE RESIN WITH VARIOUS SUBSTITUENTS AND METHOD FOR PREPARING THE SAME

(75) Inventors: Wen-Chiung Su, Longtan Township, Taoyuan County (TW); Ching-Hsuan Lin, Taichung (TW); Po-Wen Cheng, Yuli Township, Hualien County (TW)

(73) Assignee: Chung-Shan Institute of Science and Technology, Armaments Bureau, Ministry of National Defense, Taoyuan County (TW)

( * ) Notice: Subject to any disclaimer, the term of this patent is extended or adjusted under 35 U.S.C. 154(b) by 201 days.

(21) Appl. No.: 12/710,623

(22) Filed: Feb. 23, 2010

(65) Prior Publication Data

US 2011/0207908 A1  Aug. 25, 2011

(51) Int. Cl.
  *C08G 79/04*  (2006.01)
(52) U.S. Cl. ............................... 544/73; 528/44
(58) Field of Classification Search ....... 544/73
  See application file for complete search history.

(56) References Cited

U.S. PATENT DOCUMENTS

7,781,561 B2 * 8/2010 Lin et al. ............ 528/243

\* cited by examiner

*Primary Examiner* — Kahsay T Habte (57) ABSTRACT

The present invention provides a method for preparing a phosphorus-containing bexzoxazine resin having the following structure shown as the formula (I) or (V):

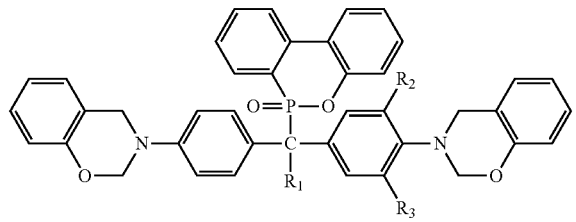

(I)

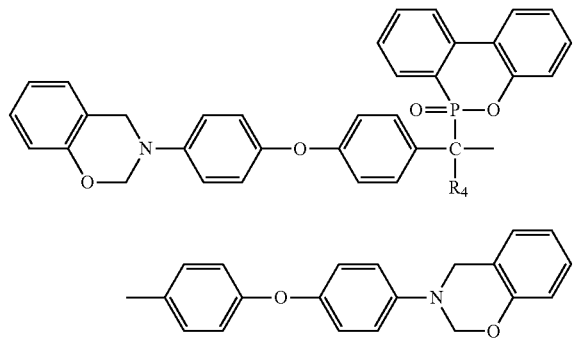

(V)

wherein, R1~R4 respectively comprise one selected from the group consisting of hydrogen, C1~C6 alkyl, C3~C6 cyclic alkyl, and phenyl.

8 Claims, 2 Drawing Sheets

PHOSPHORUS-CONTAINING BENZOXAZINE RESIN WITH VARIOUS SUBSTITUENTS AND METHOD FOR PREPARING THE SAME

BACKGROUND OF THE INVENTION

1. Field of the Invention

The invention relates to a method for preparing a phosphorus-containing benzoxazine resin, and particularly, the invention relates to a method for preparing a benzoxazine resin with high degree of purity and high yield from phosphorus-containing diamine.

2. Description of the Prior Art

Phenolic novolac resin is the thermosetting resin usually used nowadays, and it is obtained by the condensation polymerization of phenol monomer and formaldehyde monomer. The benzoxazine resin developed in the present days belongs to a type of phenolic novolac resin and the monomer of the bexzoxazine resin decyclizes and hardens after heating. Compared to the traditional phenolic novolac resin, the benzoxazine resin has the advantages of high glass transition temperature, high modulus, low hygroscopicity, high char yield, no catalyst needed, no by-product, and small variation of volume during hardening.

However, the compositions of phenolic novolac resin are carbon, hydrogen, and oxygen, and the compositions have disadvantage of ignition for the application. With the development of the electronic industry, the product tends to miniaturization. Therefore, the traditional pin through hole (PTH) technology is replaced by the surface mount technology (SMT), such as Ball Grid Array (BGA), flip chip package, and chip size package (CSP), so as to promote the printed circuit board toward high density and multi-layer. Besides, the demands of the resistance against high temperature and ignition on the materials of the semiconductor industry rise, such as the standard UL-94 V-0 of the electronic material, so that the electronic materials tend to be difficult to ignite.

The ignition resistant benzoxazine resin on the market needs carbon fibers added in the resin to increase the resistance against ignition. However, the benzoxazine resin is still not efficient for resisting against ignition, so that the igniting problem of the benzoxazine resin becomes an important issue for the electronic industry. Savants from all circles keep focusing on the resistance against ignition of the polymer material, and a contention that alkyne, deoxybenzin, or phosphorus-containing material can increase the resistance against ignition of the polymer material has been brought up.

It is obvious that most of bifunctional benzoxazine resin is made through bisphenol, single-functional amine monomer, and formaldehyde. Therefore, the elements having the flame retardancy can be added in the bisphenol or the single-functional amine, such as bisphenol monomer having phosphoryl bond or the derivatives of DOPO to achieve the purpose of increasing the resistance against ignition of the benzoxazine resin.

There are few documents describing the bifunctional benzoxazine monomer whose matrix is diamine. The reason is that the gel phenomenon occurs when the bifunctional benzoxazine monomer is synthesized from diamine through the traditional path. When the diamine reacts with the formaldehyde and the phenol, the diamine and the formaldehyde react to obtain an intermediate of triazine which is insolvable, so that the synthesis of the benzoxazine monomer whose matrix is diamine can not proceed successfully.

SUMMARY OF THE INVENTION

Therefore, the invention provides a novel means for synthesizing the benzoxazine monomer whose matrix is diamine for solving the above-mentioned problem. On the other hand, because of the demands of the resistance against high temperature and ignition on the material of the semiconductor industry, the phosphorus-containing functional group, such as a series of phosphorus-containing diamine with different substituents, is added in the construction of the diamine to synthesize the flame retardant benzoxazine resin.

A scope of the invention is to provide a phosphorus-containing benzoxazine resin which includes a structure shown as the formula (I):

(I)

wherein, R1~R3 respectively comprise one selected from the group consisting of hydrogen, C1~C6 alkyl, C3~C6 cyclic alkyl, and phenyl. According to an embodiment, when R1 of the structure shown as the formula (I) is methyl and R2 and R3 are hydrogen, the structure shown as the formula (I) becomes:

(I-A)

According to another embodiment, when R1, R2, and R3 of the structure shown as the formula (I) are methyl, the structure shown as the formula (I) becomes:

(I-B)

According to another embodiment, when R1 of the structure shown as the formula (I) is methyl and R2 and R3 are ethyl, the structure shown as the formula (I) becomes:

(I-C)

According to another embodiment, when R1 of the structure shown as the formula (I) is phenyl and R2 and R3 are hydrogen, the structure shown as the formula (I) becomes:

(I-D)

A scope of the invention is to provide a phosphorus-containing benzoxazine resin which includes a structure shown as the formula (V):

Another scope of the invention is to provide a method for preparing a phosphorus-containing benzoxazine resin.

According to an embodiment, the method for preparing the phosphorus-containing bifunctional benzoxazine resin synthesizes the phosphorus-containing benzoxazine by utilizing phosphorus-containing diamine as the matrix. The structure of the phosphorus-containing diamine is shown as followings:

(IV)

The phosphorus-containing diamine (IV) and the 2-hydroxybenzaldehyde are processed through a series of reactions to obtain the phosphorus-containing benzoxazine with different structures. In the embodiment, the method can include the following third stages.

In a first stage, the phosphorus-containing diamine (IV) and the 2-hydroxybenzaldehyde are dissolved in a mixing solvent; a Dean-Stark device is set to execute a draining reaction at the reflux temperature and an intermediate (III) having an imine band is generated; and, then a hydrophobic solvent is removed from the mixing solvent. After the first stage finishes and the temperature reduces to the room temperature, a second stage proceeds.

(V)

wherein, R4 comprises one selected from the group consisting of hydrogen, C1~C6 alkyl, C3~C6 cyclic alkyl, and phenyl.

According to an embodiment, when R4 of the structure shown as the formula (V) is methyl, the structure shown as the formula (V) becomes:

The mixing solvent used in the first stage can include DMAC/Toluene, NMP/Toluene, DMSO/Toluene, DMF/Xylene, DMAC/Xylene, NMP/Xylene, or DMSO/Xylene. The hydrophobic solvent includes Toluene and Xylene.

In the second stage, $NaBH_4$ is mixed in the reacting system in the first stage to react at a room temperature after the first (V-A)

stage finishes and the reflux temperature drops to the room temperature, and then the reacting liquid is mixed in the water to separate an intermediate (II).

In a third stage, the intermediate (II) is dissolved in a solvent; a formaldehyde solution or a paraformaldehyde is mixed in the solution with the intermediate (II) to stir for a duration at a temperature of 35° C., and then the temperature is raised to a reflux temperature from 35° C.; and, the solvent is removed by a spin concentrator to obtain the final product (I). The solvent in the third stage can include Toluene, Xylene, $CHCl_3$, or Dioxane.

According to this embodiment, the three stages above-mentioned can be shown in chemical formula as followings:

wherein, R1 includes one selected from the group consisting of C1~C6 alkyl, C3~C6 cyclic alkyl, and phenyl, and R2~R3 respectively include one selected from the group consisting of hydrogen, C1~C6 alkyl, C3~C6 cyclic alkyl, and phenyl.

According to another embodiment of the invention, the phosphorus-containing benzoxazine having ether base can be synthesized by utilizing phosphorus-containing diether-amine as the matrix. The structure of the phosphorus-containing diether-amine is shown as followings:

(VIII)

wherein, R4 includes one selected from the group consisting of hydrogen, C1~C6 alkyl, C3~C6 cyclic alkyl, and phenyl.

The method for preparing the phosphorus-containing benzoxazine through the phosphorus-containing diether-amine (VIII) can also include three stages. In a first stage, the phosphorus-containing diether-amine (VIII) and the 2-hydroxybenzaldehyde are dissolved in a mixing solvent; a Dean-Stark device is set to execute a draining reaction at the reflux temperature and an intermediate (III) having an imine band is generated; and, then a hydrophobic solvent is removed from the mixing solvent. After the first stage finishes and the temperature reduces to the room temperature, a second stage proceeds.

The mixing solvent used in the first stage can include DMAC/Toluene, NMP/Toluene, DMSO/Toluene, DMF/Xylene, DMAC/Xylene, NMP/Xylene, or DMSO/Xylene. The hydrophobic solvent includes Toluene and Xylene.

In the second stage, $NaBH_4$ is mixed in the reacting system in the first stage to react at a room temperature after the first stage finishes and the reflux temperature drops to the room temperature, and then the reacting liquid is mixed in the water to separate an intermediate (VI).

In a third stage, the intermediate (VI) is dissolved in a solvent; a formaldehyde solution or a paraformaldehyde is mixed in the solution with the intermediate (II) to stir for a duration at a temperature of 35° C., and then the temperature is raised to a reflux temperature from 35° C.; and, the solvent is removed by a spin concentrator to obtain the final product (V). The solvent in the third stage can include Toluene, Xylene, $CHCl_3$, or Dioxane.

According to this embodiment, the three stages above-mentioned can be shown in chemical formula as followings:

(V)

wherein, R4 includes one selected from the group consisting of hydrogen, C1~C6 alkyl, C3~C6 cyclic alkyl, and phenyl.

These and other features, aspects, and advantages of the present invention will become better understood with regard to the following description, appended claims, and accompanying drawings.

DETAILED DESCRIPTION OF THE INVENTION

According to an embodiment of the invention, the method for preparing the phosphorus-containing benzoxazine resin is shown in Flow Chart 1, and then the detail about Flow Chart 1 will be described in the followings.

Flow Chart 1

Example 1

The Synthesis of the Compound (I-A)

21.32 g (0.05 moles) Phosphorus-containing diamine monomer (IV-A) and 12.82 g (0.105 moles) 2-hydroxybenzaldehyde are dissolved in DMAc/Toluene. The solution is contained in a three-necked bottle and a Dean-Stark device is set to execute a draining reaction. The reaction proceeds at the reflux temperature for 12 hours. After the reaction finishes, Toluene is removed from the solution and the reflux temperature drops to the room temperature. $NaBH_4$ are added into the three-necked bottle in batches and then the solution is stirred at the room temperature for 24 hours. After the reaction finishes, the reacting liquid is mixed in the deionized water to separate a white powder. The pumping and filtering process is used for obtain the white powder (II-A) 30.33 g, and the yield is 95%.

Figure 1:
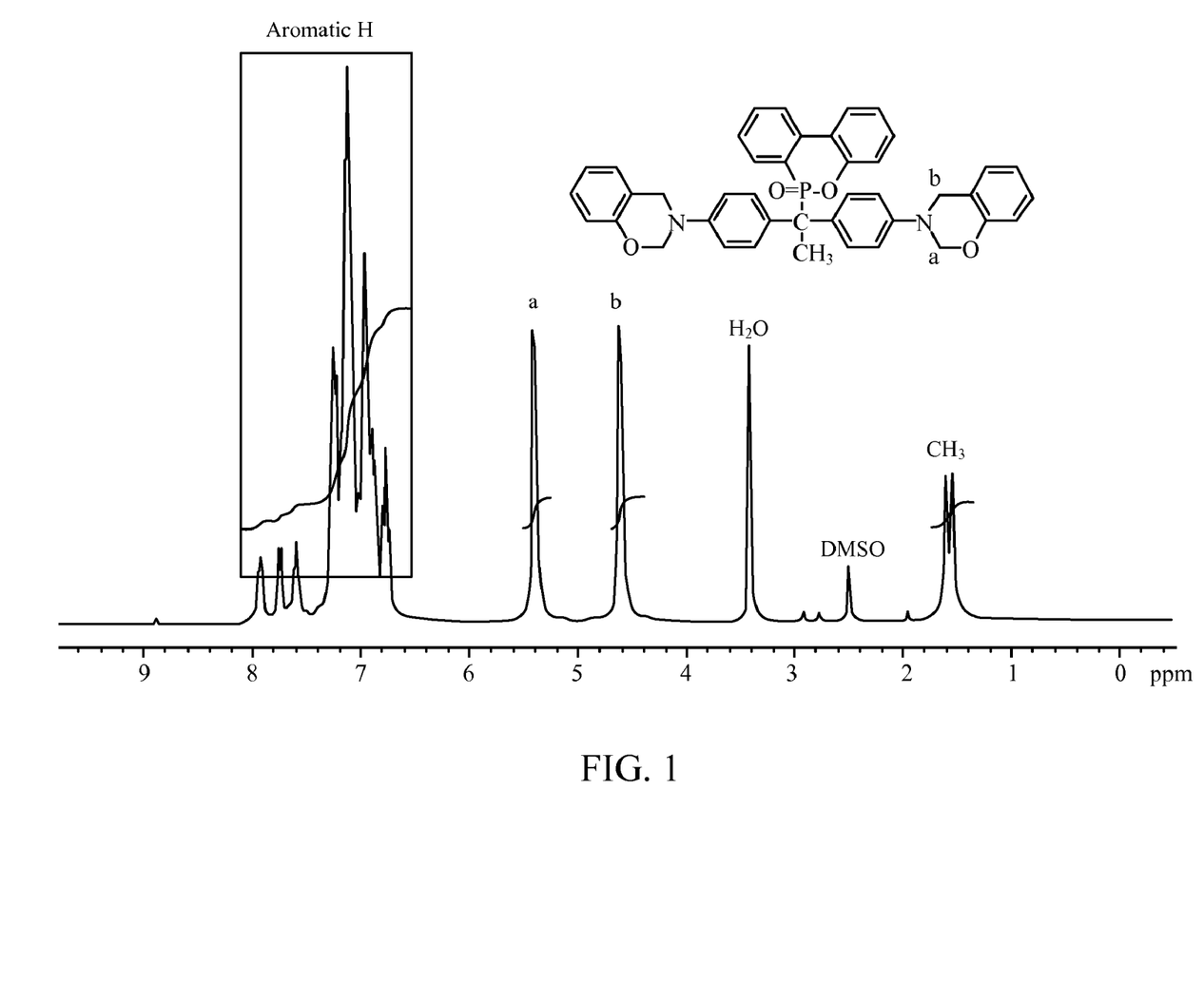
FIG. 1 is a schematic diagram illustrating 1H NMR spectrum of the compound (I-A).

Afterwards, 10.0 g (0.0156 moles) monomer (II-A) is dissolved in Toluene, and then 1.4976 g (0.0499 moles) paraformaldehyde is added into the three-necked bottle to react at the reflux temperature for 24 hours. After the reaction finishes, Toluene is removed by a spin concentrator to obtain a light yellow powder (I-A) 10.27 g, and the yield is 99%. Please refer to FIG. 1. FIG. 1 is a schematic diagram illustrating 1H NMR spectrum of the compound (I-A).

Example 2

The Synthesis of the Compound (I-B)

22.73 g (0.05 moles) Phosphorus-containing diamine monomer (IV-A) and 12.82 g (0.105 moles) 2-hydroxybenzaldehyde are dissolved in DMAc/Toluene. The solution is contained in a three-necked bottle and a Dean-Stark device is set to execute a draining reaction. The reaction proceeds at the reflux temperature for 12 hours. After the reaction finishes, Toluene is removed from the solution and the reflux temperature drops to the room temperature. $NaBH_4$ are added into the three-necked bottle in batches and then the solution is stirred at the room temperature for 24 hours. After the reaction finishes, the reacting liquid is mixed in the deionized water to separate a white powder. The pumping and filtering process is used for obtain the white powder (II-B) 30.33 g, and the yield is 91%.

Afterwards, 10.0 g (0.0149 moles) monomer (II-B) is dissolved in Toluene, and then 1.437 g (0.0479 moles) paraformaldehyde is added into the three-necked bottle to react at the reflux temperature for 24 hours. After the reaction finishes, Toluene is removed by a spin concentrator to obtain a light yellow powder (I-B) 10.09 g, and the yield is 98%.

Example 3

The Synthesis of the Compound (I-C)

24.123 g (0.05 moles) Phosphorus-containing diamine monomer (IV-C) and 12.82 g (0.105 moles) are dissolved in DMAc/Toluene. The solution is contained in a three-necked bottle and a Dean-Stark device is set to execute a draining reaction. The reaction proceeds at the reflux temperature for 12 hours. After the reaction finishes, Toluene is removed from the solution and the reflux temperature drops to the room temperature. NaBH$_4$ are added into the three-necked bottle in batches and then the solution is stirred at the room temperature for 24 hours. After the reaction finishes, the reacting liquid is mixed in the deionized water to separate a white powder. The pumping and filtering process is used for obtain the white powder (II-C) 32.66 g, and the yield is 94%.

Afterwards, 10.0 g (0.0143 moles) monomer (II-C) is dissolved in Toluene, and then 1.381 g (0.046 moles) paraformaldehyde is added into the three-necked bottle to react at the reflux temperature for 24 hours. After the reaction finishes, Toluene is removed by a spin concentrator to obtain a light yellow powder (I-C) 10.14 g, and the yield is 98%.

Example 4

The Synthesis of the Compound (I-D)

24.426 g (0.05 moles) Phosphorus-containing diamine monomer (IV-D) and 12.82 g (0.105 moles) are dissolved in DMAc/Toluene. The solution is contained in a three-necked bottle and a Dean-Stark device is set to execute a draining reaction. The reaction proceeds at the reflux temperature for 12 hours. After the reaction finishes, Toluene is removed from the solution and the reflux temperature drops to the room temperature. NaBH$_4$ are added into the three-necked bottle in batches and then the solution is stirred at the room temperature for 24 hours. After the reaction finishes, the reacting liquid is mixed in the deionized water to separate a white powder. The pumping and filtering process is used for obtain the white powder (II-D) 32.2 g, and the yield is 92%.

Figure 2:
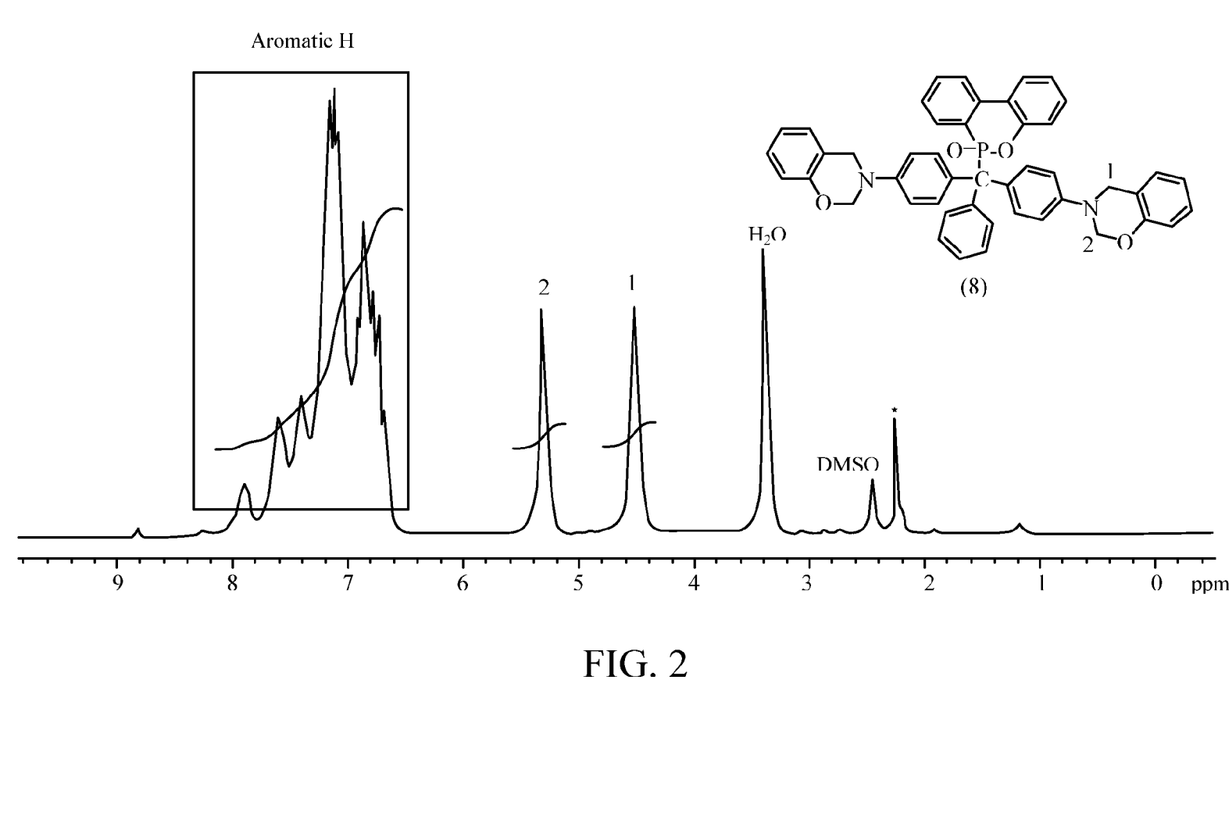
FIG. 2 is a schematic diagram illustrating 1H NMR spectrum of the compound (I-D).

Afterwards, 10.0 g (0.0142 moles) monomer (II-D) is dissolved in Toluene, and then 1.37 g (0.0454 moles) paraformaldehyde is added into the three-necked bottle to react at the reflux temperature for 24 hours. After the reaction finishes, Toluene is removed by a spin concentrator to obtain a light yellow powder (I-D) 10.291 g, and the yield is 99%. Please refer to FIG. 2. FIG. 2 is a schematic diagram illustrating 1H NMR spectrum of the compound (I-D).

According to another embodiment of the invention, the method for preparing the phosphorus-containing benzoxazine resin is shown in Flow Chart 2, and then the detail about Flow Chart 2 will be described in the followings.

Flow Chart 2

Example 5

The Synthesis of the Compound (V-A)

30.53 g (0.05 moles) Phosphorus-containing diamine monomer (VIII-A) and 12.82 g (0.105 moles) are dissolved in DMAc/Toluene. The solution is contained in a three-necked bottle and a Dean-Stark device is set to execute a draining reaction. The reaction proceeds at the reflux temperature for 12 hours. After the reaction finishes, Toluene is removed from the solution and the reflux temperature drops to the room temperature. NaBH$_4$ are added into the three-necked bottle in batches and then the solution is stirred at the room temperature for 24 hours. After the reaction finishes, the reacting liquid is mixed in the deionized water to separate a white powder. The pumping and filtering process is used for obtain the white powder (VI-A) 38.26 g, and the yield is 93%.

Afterwards, 10.0 g (0.012 moles) monomer (VI-A) is dissolved in Toluene, and then 1.16 g (0.0388 moles) paraformaldehyde is added into the three-necked bottle to react at the reflux temperature for 24 hours. After the reaction finishes, Toluene is removed by a spin concentrator to obtain a light yellow powder (V-A) 10.084 g, and the yield is 98%.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A phosphorus-containing benzoxazine resin of a structure shown as a formula (I):

(I)

wherein, R1~R3 respectively comprise one selected from the group consisting of hydrogen, C1-C6 alkyl, C3~C6 cyclic alkyl, and phenyl.

2. A phosphorus-containing benzoxazine resin of a structure shown as a formula (V):

wherein, R4 is one selected from the group consisting of hydrogen, C1~C6 alkyl, C3~C6 cyclic alkyl, and phenyl.

3. A method for preparing a phosphorus-containing benzoxazine resin, the phosphorus-containing benzoxazine resin of a structure shown as a formula (I):

(I)

the method comprising the following steps:

(a) in a first stage, dissolving phosphorus-containing diamine and 2-hydroxybenzaldehyde in a mixing solvent, setting a Dean-Stark device to execute a draining reaction at the reflux temperature, generating an intermediate (III) having an imine band, and removing a hydrophobic solvent from the mixing solvent;

(b) in a second stage, mixing NaBH$_4$ in the reacting system in the first stage to react at a room temperature after the first stage finishes and the reflux temperature drops to the room temperature, and then mixing the reacting liquid in the water to separate an intermediate (II); and (c) in a third stage, dissolving the intermediate (II) in a solvent, mixing a formaldehyde solution or a paraformaldehyde in the solution with the intermediate (II) to stir for a duration at a temperature of 35° C., raising the temperature to a reflux temperature from 35° C., and removing the solvent by a spin concentrator to obtain the phosphorus-containing benzoxazine resin comprising the structure shown as the formula (I).

4. The method according to claim 3, wherein the mixing solvent in the step (a) is at least one selected from the group consisted of DMAC/Toluene, NMP/Toluene, DMSO/Toluene, DMAC/Xylene, NMP/Xylene, and DMSO/Xylene, and the hydrophobic solvent comprises Toluene and Xylene.

5. The method according to claim 3, wherein the solvent in the step (c) is at least one selected from the group consisted of Toluene, Xylene, CHCl$_3$, and Dioxane.

6. A method for preparing a phosphorus-containing benzoxazine resin, the phosphorus-containing benzoxazine resin of a structure shown as a formula (V):

(V)

(V)

the method comprising the following steps:
(a) in a first stage, dissolving phosphorus-containing diether-amine (VIII) and 2-hydroxybenzaldehyde in a mixing solvent, setting a Dean-Stark device to execute draining reaction at the reflux temperature, generating an intermediate (VII) having an imine band, and removing a hydrophobic solvent from the mixing solvent;
(b) in a second stage, mixing NaBH$_4$ in the reacting system in the first stage to react at a room temperature after the first stage finishes and the reflux temperature drops to the room temperature, and then mixing the reacting liquid in the water to separate an intermediate (VI); and
(c) in a third stage, dissolving the intermediate (VI) in a solvent, mixing a formaldehyde solution or a paraformaldehyde in the solution with the intermediate (II) to stir for a duration at a temperature of 35° C., raising the temperature to a reflux temperature from 35° C., and removing the solvent by a spin concentrator to obtain the phosphorus-containing benzoxazine resin comprising the structure shown as the formula (V).

7. The method according to claim 6, wherein the mixing solvent in the step (a) is at least one selected from the group consisted of DMAC/Toluene, NMP/Toluene, DMSO/Toluene, DMAC/Xylene, NMP/Xylene, and DMSO/Xylene, and the hydrophobic solvent comprises Toluene and Xylene.

8. The method according to claim 6, wherein the solvent in the step (c) is at least one selected from the group consisted of Toluene, Xylene, CHCl$_3$, and Dioxane.

* * * * *